United States Patent
Bayod Jasanada et al.

(10) Patent No.: US 6,451,990 B1
(45) Date of Patent: Sep. 17, 2002

(54) AZITHROMYCIN PREPARATION IN ITS NONCRYSTALLINE AND CRYSTALLINE DIHYDRATE FORMS

(75) Inventors: Miguel Santos Bayod Jasanada; Isidro Llorente Garcia; Felix Fernandex Mari, all of Asturias (ES)

(73) Assignee: Astur-Pharma, S.A., Madrid (ES)

( * ) Notice: Subject to any disclaimer, the term of this patent is extended or adjusted under 35 U.S.C. 154(b) by 0 days.

(21) Appl. No.: 09/718,833

(22) Filed: Nov. 22, 2000

(30) Foreign Application Priority Data

Nov. 26, 1999 (ES) ................................. 9902620

(51) Int. Cl.[7] ................................................ C07H 1/00
(52) U.S. Cl. ........................................ 536/7.4; 536/18.5
(58) Field of Search .................... 536/7.4, 18.5

(56) References Cited

U.S. PATENT DOCUMENTS

| | | |
|---|---|---|
| 4,474,768 A | 10/1984 | Bright |
| 4,517,359 A | 5/1985 | Kobrehel et al. |
| 5,686,587 A | 11/1997 | Yang |
| 5,869,629 A | 2/1999 | Bayod Jasanda et al. |
| 6,245,903 B1 * | 6/2001 | Karimian et al. ............ 536/7.4 |

FOREIGN PATENT DOCUMENTS

| | | |
|---|---|---|
| EC | SP 95-1389 | 5/1995 |
| EP | 0 941 999 A2 | 9/1999 |
| WO | WO 89/00576 | 1/1989 |

OTHER PUBLICATIONS

*Chemical Abstracts—26—Biomolecules and Their Synthetic Analogs*, vol. 124, No. 3, 1996, 29525q, Q. Song, et al. "Preparation of crystals of azithromycin via crystalization from various solvents."

*J. Chem. Research* (S), 1988, 152–153, "Erythromycin Series. Part 13. Synthesis and Structure Elucidation of 10–Dihydro–10–deoxo–11–methyl–11–azaerythromycin A", Slobodan Djokić, et al.

*J. Org. Chem*, American Chemical Society, 1997, "Synthesis of 9–deoxo–9a–aza–9a–homoerythromycin A 11, 12–Hydrogen Borate and Azithromycin 11, 12–Hydrogen Borate. A new Procedure to Obtain Azithromycin Dihydrate" by M. Bayod–Jasanada, et al.

\* cited by examiner

*Primary Examiner*—Elli Peselev
(74) *Attorney, Agent, or Firm*—Knobbe, Martens, Olson & Bear, LLP

(57) ABSTRACT

The present invention describes new procedures for the preparation of the macrolide azithromycin in its non-crystalline and crystalline dihydrate forms, which are characterized and clearly differentiated by means of the following methods and techniques:

1. IR Spectroscopy.
2. Differential Scan Calorimetry (DSC).
3. X-Ray Diffraction.
4. Hygroscopicity.
5. Crystallinity test (Light Polarized Microscopy)

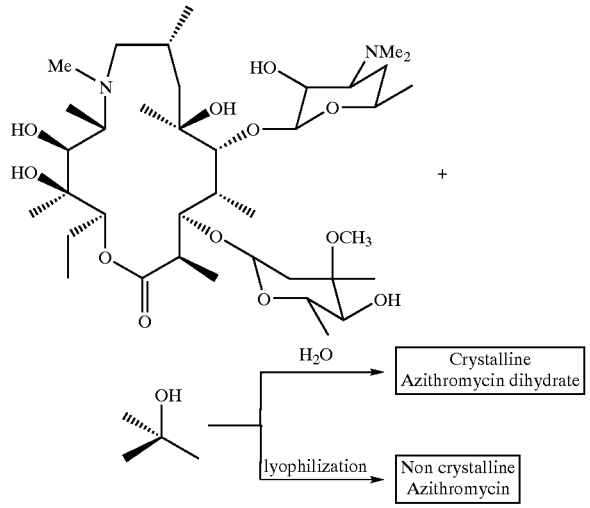

18 Claims, 4 Drawing Sheets

Figure 1 : Synthesis of Azithromycin

Figure 2
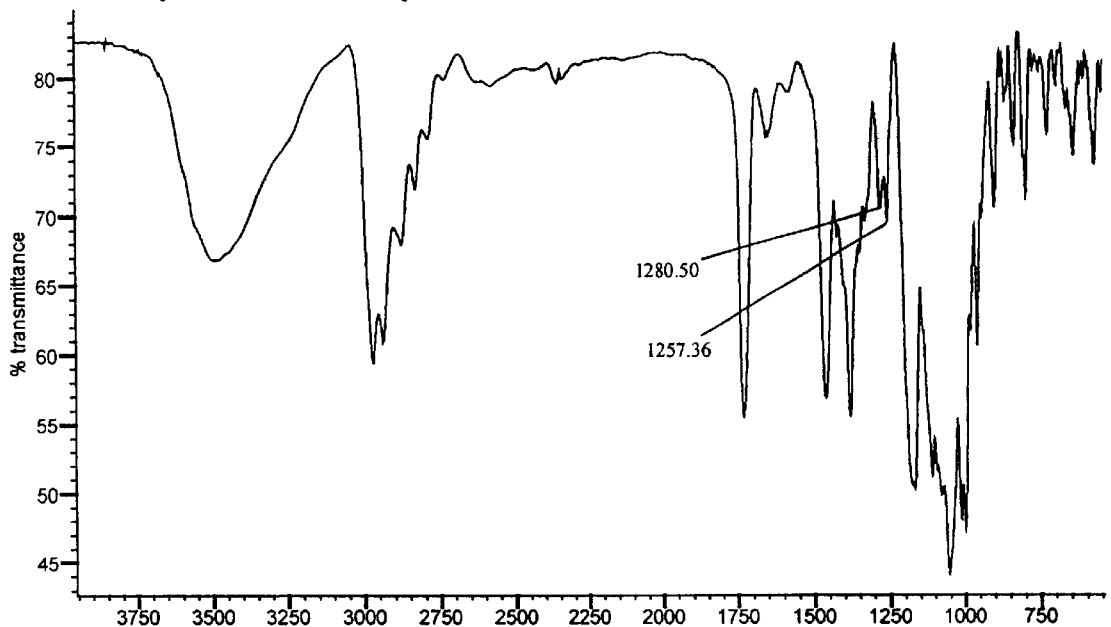
Non crystalline Azithromycin
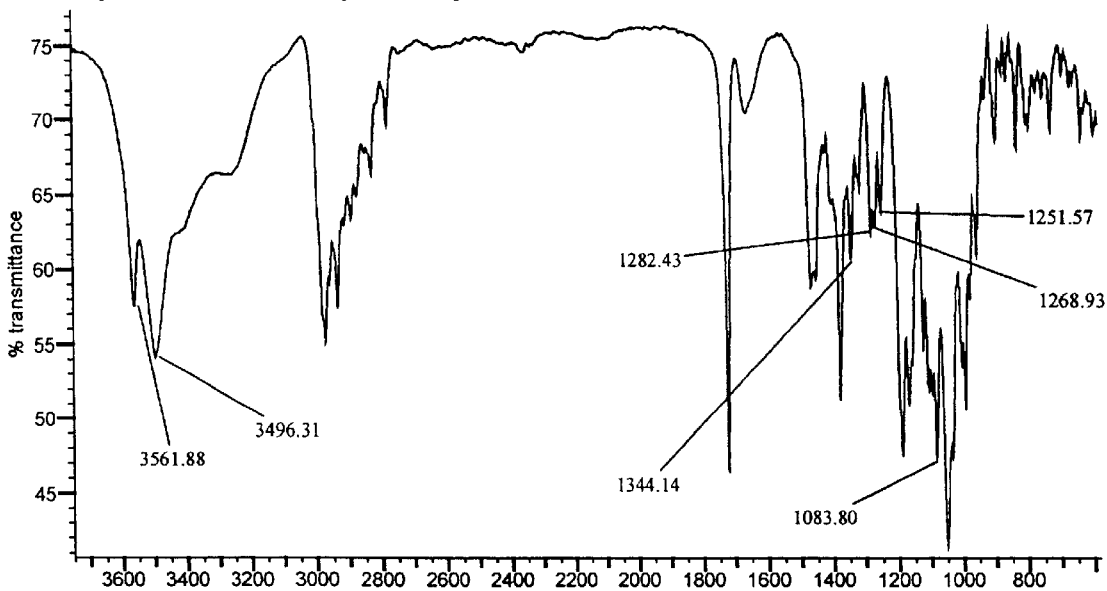
Crystalline Azithromycin dihydrate

Figure 3
Thermogram of non crystalline Azithromycin
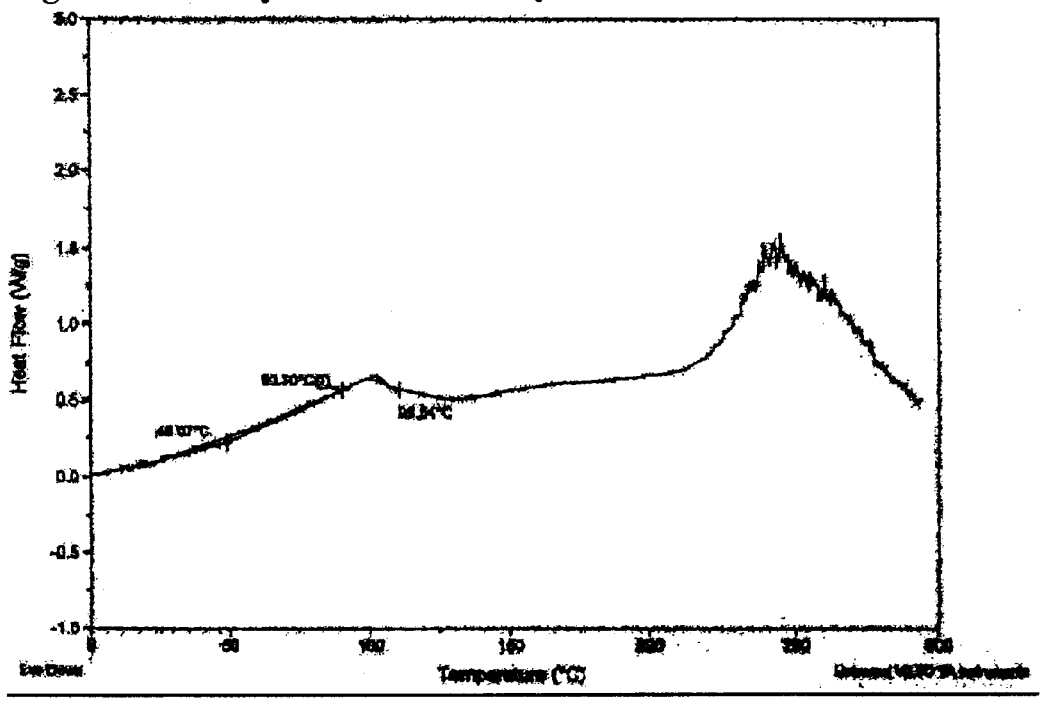
Thermogram of crystalline Azithromycin dihydrate
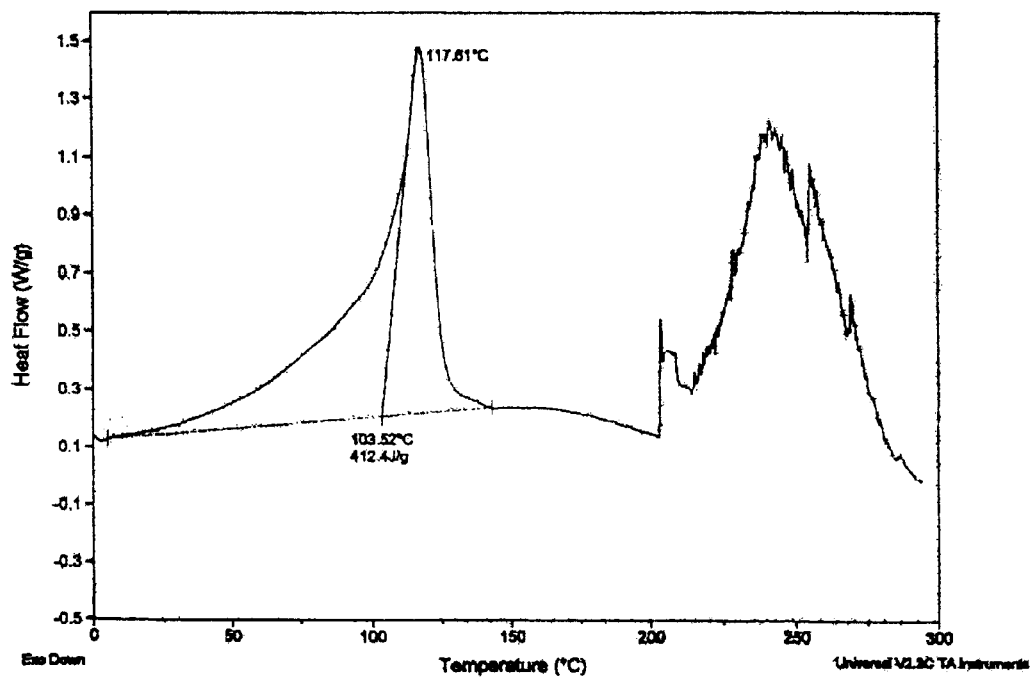

Figure 4
Non crystalline Azithromycin
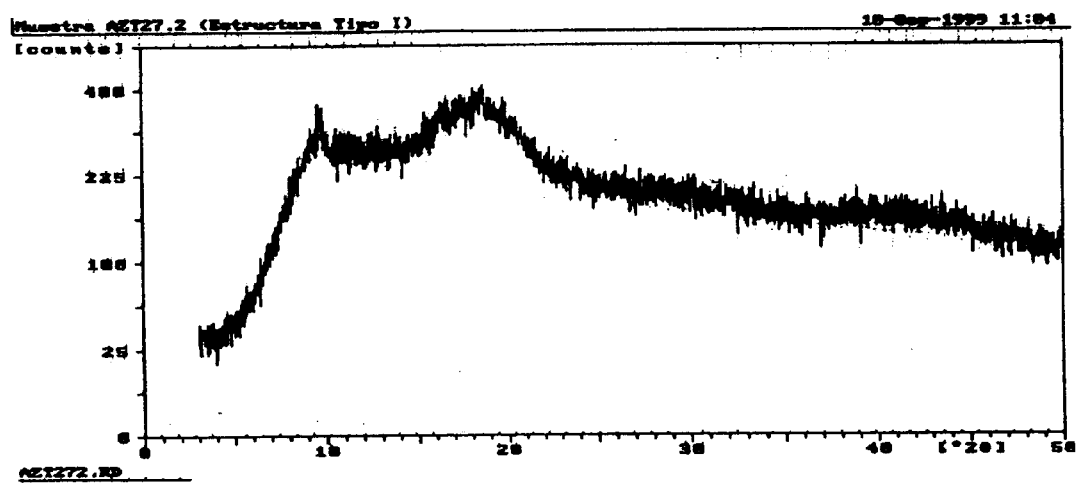
Crystalline Azithromycin dihydrate
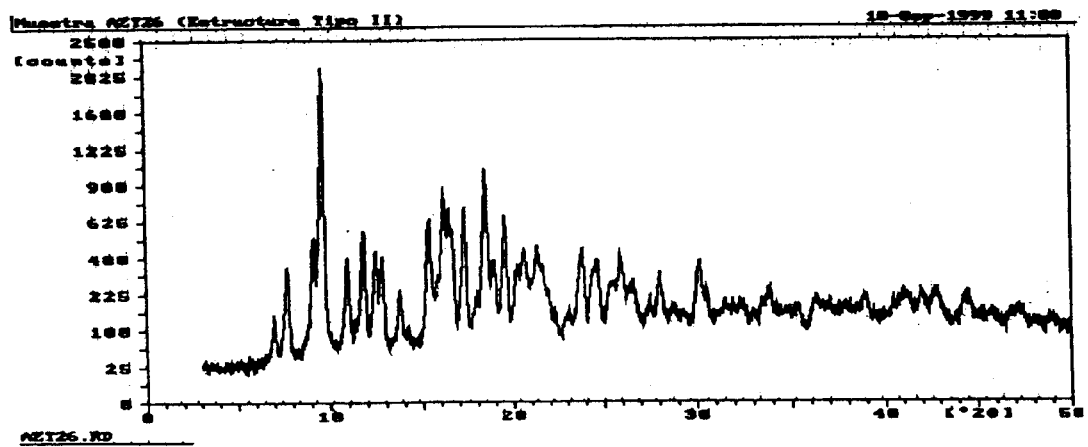

AZITHROMYCIN PREPARATION IN ITS NONCRYSTALLINE AND CRYSTALLINE DIHYDRATE FORMS

BACKGROUND OF THE INVENTION

1. Field of the Invention

Azithromycin is the USAN generic name of the azalide 9-deoxo-9a-aza-9a-methyl-9a-homoerythromycin A, which systematic name is 1-oxa-6-azacyclopentadecan-15-one, 13-((2,6-dideoxy-3-C-methyl-1-3-O-methyl-alpha-L-ribo-hexopyranosyl)-oxy)-2-10 ethyl-3,4,1 0-trihydroxy-3,5,6,8,10,12,14-heptamethyl-11-((3,4,6-trideoxy-3-(dimethyl-amino)-beta-D-xyl It is a semisynthetic macrolide that shows an excellent antimicrobial activity against gram-positive and some cases of gram-negative bacteria (H. A. Kirst, G. D. Sides, *Antimicrob. Agents. Chemother.* 1989, 33, 1419–1422). Clinical use of this macrolide is broadening its application to the treatment of opportunistic infections (F. Lecomte, *Rev. Med Interne* 1998, 19(4), 255–61; S. Alvarez-Elcoro, *Mayo Clin. Proc.* 1999, 74(6), 613–34; J. Schater, Lancet, 1999, 354(9179), 630–35).

2. Description of the Prior Art

FIG. 1 shows the different synthetic routes to azithromycin 1. The names of the intermediates displayed in FIG. 1 are gathered in the following table.

| Intermediate | Name |
|---|---|
| 1 | Azithromycin |
| 2 | Erythromycin A oxime |
| 3 | 6,9-iminoether |
| 4 | 9,11-iminoether |
| 5 | Azaerythromycin A |
| 6 | Azaerythromycin 11,12-hydrogenorthoborate |
| 7 | Azithromycin 11,12-hydrogenorthoborate |

The following table summarizes the patents, articles, authors and applicants that describe the different synthetic paths (A, B, C, D, E) towards azithromycin 1.

| Route | Patents | Articles | Author | Applicant |
|---|---|---|---|---|
| A | a) U.S. 4,328,334<br>U.S. 4,517,359 | J. Chem. Soc. Perkin Trans I, 1986, 1881<br>J. Chem. Res., 1988, 132<br>Idem miniprint., 1988, 1239 | S. Djokic | PLIVA |
| B | b) U.S. 4,474,768 | | G. M. Bright | PFIZER |
| C | c) U.S. 5,686,587<br>d) EP 0,699,207<br>e) ES 2,104,386 | | B. V. Yang | PFIZER |
| D | f) U.S. 5,869,629<br>g) EP 0,827,965<br>h) ES 2,122,905 | J. Org. Chem, 1997, 62, (21), 7479–7481<br>Magn. Reson. Chem, 1998, 36, 217–225 | M. Bayod | ASTUR PHARMA |
| E | i) EP 0,879,823 | | W. Heggie | HOVIONE |

The structural elucidation studies carried out with azithromycin 1 have shown the existence of two different crystalline forms: hygroscopic monohydrate and non-hygroscopic dihydrate, being the latter preferred for manufacturing formulations used in therapeutical treatments, as it is described in EP 0,298,650.

Azithromycin dihydrate is easily distinguishable from hygroscopic azithromycin by means of the following differentiative assays:

a) The dihydrate form keeps its percentile water content constant at values (4.5–5%) which are very close to the theoretical value (4.6%).

b) The differential calorimetry analysis (DSC) of azithromycin dihydrate reveals the presence of a single endotherm which may vary between 115 and 135° C., with an energy absorbed during the process which ranges between 27 and 34 cal/g.

c) Each crystalline form presents its own characteristic X-Ray Diffraction spectrum d) The infrared spectra in KBr of both crystalline forms present clear differences:

| azithromycin dihydrate<br>$v(cm^{-1})$ | azithromycin monohydrate<br>$v(cm^{-1})$ |
|---|---|
| 3560 and 3496 (2 sharp bands) | 3500 (wide band) |
| 1344 | Does not present any |
| 1282 and 1268 (2 sharp bands) | 1280 |
| 1083 | Does not present any |

Two other synthesis, affording azithromycin 1 as a form that should differ from the crystalline ones previously mentioned, have also been described. In these cases, azithromycin is obtained by simple evaporation to dryness. However, in these documents there is no reference to the crystalline state of the azithromycin thus obtained.

| Patent | Applicant<br>(Author) | Priority | Procedure |
|---|---|---|---|
| WO 94/26758<br>a) U.S. 5,686,587<br>b) EP 0,699,207<br>c) ES 2,104,386 | PFIZER<br>(B. V. Yang) | May 19, 1993 | Methylene chloride evaporation |
| BE 892,357<br>U.S. 4,517,359 | PLIVA<br>(S. Djokic) | Mar. 3, 1981 | Chloroform evaporation |

In the following table are summarized the different procedures for the preparation of both crystalline forms of azithromycin 1.

| Crystalline form | Patent | Applicant (Author) | Priority | Procedure |
|---|---|---|---|---|
| HYGROSCOPIC MONOHYDRATE | a) EP 0,101,186 b) U.S. 4,474,768 | PFIZER (G. M. Bright) | July 19, 1982 | Recrystallization from ethanol/water |
| HYGROSCOPIC MONOHYDRATE | c) EP 0,298,650 | PFIZER (D. Allen) | July 9, 1997 | Recrystallization from ethanol/water |
| NON-HYGROSCOPIC DIHYDRATE | d) EP 0,298,650 e) WO 89/00576 f) ES 2,038,756 | PFIZER (D. Allen) | July 9, 1997 | Recrystallization from THF/petroleum ether/ water |
| NON-HYGROSCOPIC DIHYDRATE | g) CN 1,093,370 (Chem. Abs. 29525q, 124, 1996) | Faming Zhuanli (Q. Song) | Dec. 10, 1993 | Recrystallization from acetone/water Recrystallization from other solvents, (methanol, DMF, acetonitrile, dioxane,) and water |
| NON-HYGROSCOPIC DIHYDRATE | h) EC 95-1389 | CHEMO-TECNICA SINTYAL | May, 1995 | Recrystallization from acetone/water |
| NON-HYGROSCOPIC DIHYDRATE | i) EP 0,827,965 j) ES 2,122,905 k) U.S. 5,869,629 | ASTUR PHARMA (M. Bayod) | July 11, 1996 | Recrystallization from acetone/water |
| NON-HYGROSCOPIC DIHYDRATE | l) EP 0,941,999 | HOVIONE (W. Heggie) | Mar. 13, 1998 | Precipitation from a base neutralized acid solution of azithromycin in acetone/water |

| Crystalline form | Article | Author | Date | Procedure |
|---|---|---|---|---|
| NON-HYGROSCOPIC DIHYDRATE | J. Chem. Res., 1988, 132 m) idem miniprint., 1988, 1239, | S. Djokic (PLIVA) | May, 1988 (received June 4, 1987) | Two recrystallizations: 1. Precipitation from a base neutralized acid solution of azithromycin in acetone/water. 2. From ethyl ether. |
| NON-HYGROSCOPIC DIHYDRATE | J. Org. Chem, 1997, 62, (21), 7479–7481 | M. Bayod (ASTUR-PHARMA) | Nov., 1997 (received May 1, 1997) | Recrystallization from acentone/water |
| HYGROSCOPIC MONOHYDRATE | J. Org. Chem, 1997, 62, (21), 7479–7481 | M. Bayod (ASTUR PHARMA) | Nov., 1997 (received May 1, 1997) | Recrystallization from ethanol/water |

BRIEF DESCRIPTION OF THE DRAWINGS

FIG. 2 shows the infrared spectra of non-crystalline azithromycin and crystalline azithromycin dihydrate recorded in FT-IR Nicolet® Impact 410 Instrument.

FIG. 3 shows the thermograms of non-crystalline azithromycin and crystalline azithromycin dihydrate obtained scanning between 20 and 300° C., under nitrogen with a heating rate of 5° C./min.

FIG. 4 shows X-ray diffraction spectra of non-crystalline azithromycin and crystalline azithromycin dihydrate recorded on a Philips® PW1710 diffractometer.

Figure 1:
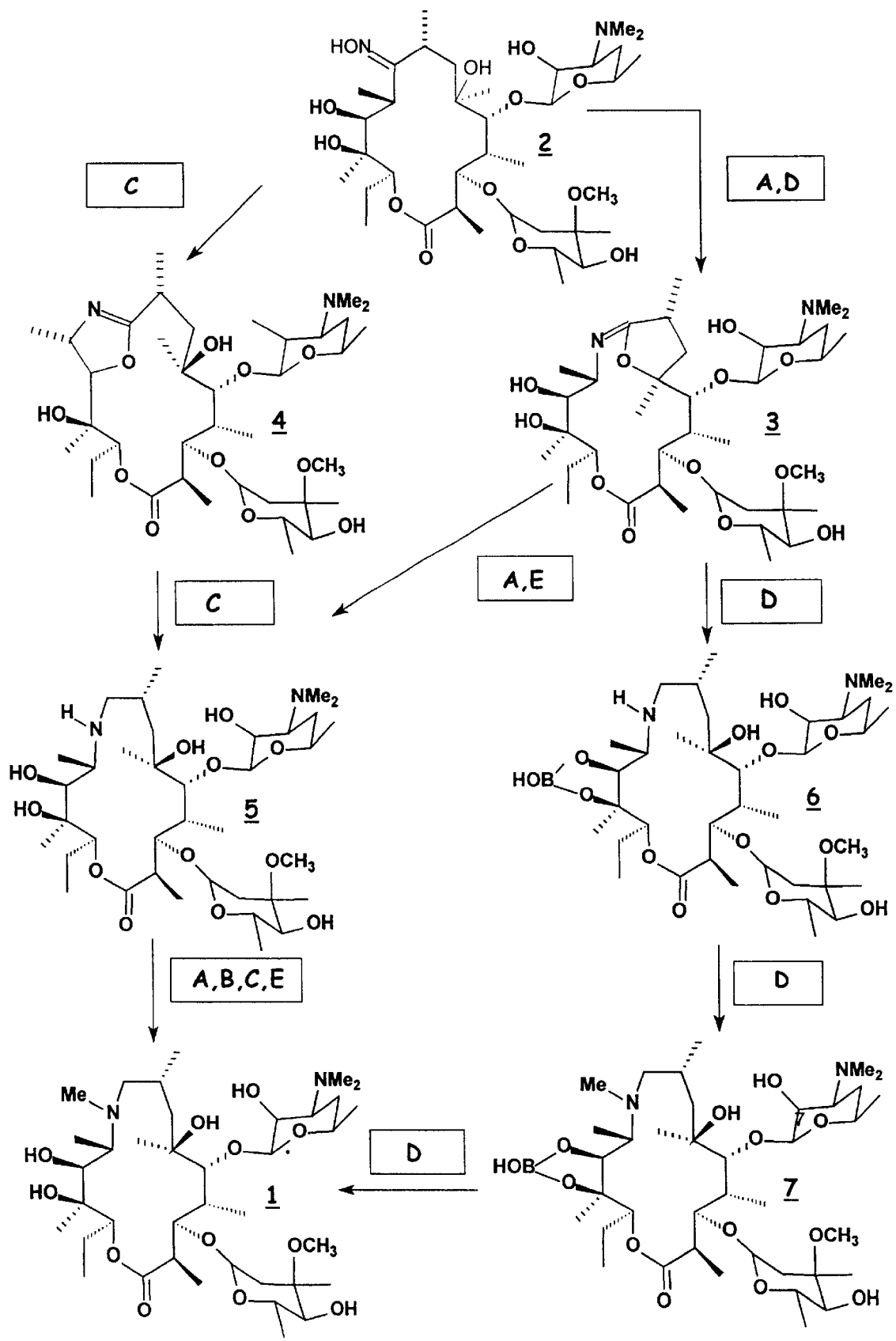
FIG. 1 shows the different synthetic routes to azithromycin.

DESCRIPTION OF THE INVENTION.

First, the present invention provides a series of new procedures for the preparation of azithromycin 1:

A procedure for the preparation of its crystalline dihydrate form, characterized by crystallization of azithromycin from a mixture of tert-butanol/water. In this procedure crystalline azithromycin monohydrate is dissolved in tert-butanol and, after water addition, is allowed to crystallize for a period of 48–72 hours.

A procedure for the preparation of its crystalline dihydrate form, characterized by crystallization of azithromycin from a mixture of tert-butanol/petroleum ether/water. In this procedure, crystalline azithromycin monohydrate is dissolved in tert-butanol and added to a mixture of petroleum ether and water. This solution is allowed to crystallize for a period of 48–72 hours.

A procedure for the preparation of non-crystalline azithromycin by means of lyophilization of solutions of azithromycin in tert-butanol (2-methyl-2-propanol).

A procedure for the preparation of non-crystalline azithromycin by means of evaporation of solutions of azithromycin in aliphatic alcohols (preferably ethanol or isopropanol).

Secondly, the present invention describes the characterization of non-crystalline azithromycin and its unambiguous differentiation from the crystalline forms (dihydrate and monohydrate) using the following techniques:

Infrared Spectroscopy

Differential Scan Calorimetry (DSC)

V X-Ray Diffraction

Hygroscopicity

Crystallinity test by means of polarized light microscopy

The procedures which are the object of the present invention are advantageous over previously described methods, essentially at industrial scale:

Lyophilization is a technique that guarantees excellent results concerning homogeneity, purity and consistency of analytical data of different batches.

The crystallization procedures, which are characterized by slow crystal growth, greatly improve the homogeneity and particle distribution of different batches. This minimizes the presence of the non-crystalline fraction (detected by X-Ray and DSC) that is always present in crystalline azithromycin dihydrate obtained by the methods reported in the literature and above cited.

The differences observed between crystalline azithromycin dihydrate and its non-crystalline form, using the techniques previously mentioned, are shown below:

1. Infrared Spectra (KBr), recorded in a FT-IR Nicolet® Impact 410 Instrument, of both azithromycin forms are clearly different. FIG. 2 reproduces the spectra which most significative bands are summarized in the following table:

| Crystalline azithromycin dihydrate $v(cm^{-1})$ | Non-crystalline azithromycin $v(cm^{-1})$ |
|---|---|
| 3561 and 3496 (2 sharp bands) | 3500 (wide band) |
| 1344 | Does not present any |
| 1282, 1269 and 1251 (3 sharp bands) | 1280 and 1257 (2 sharp bands) |
| 1083 | Does not present any |

2. DSC. In FIG. 3 are shown the thermograms obtained scanning between 20 and 300° C., under nitrogen with a heating rate of 5° C./min. The thermogram of the non-crystalline form does not present any melting peak, what clearly differentiates it from the one corresponding to crystalline azithromycin dihydrate.

3. X-Ray Diffraction Spectra were recorded on a Philips® PW1710 diffractometer. As the spectrum corresponding to non-crystalline azithromycin (FIG. 4) is characterized by the absence of defined maxima, this solid is considered to be amorphous.

4. Hygroscopicity. Two different samples of non-crystalline azithromycin containing 3% water were kept under an atmosphere over 75% relative humidity. After 8 hours, water content in the first sample was 5.3%, while the second one contained 9.9% water after 72 hours. Non-crystalline azithromycin is thus moderately hygroscopic.

5. Crystallinity tests (polarized light microscopy) carried out with non-crystalline azithromycin were negative, as their particles do not show birefringence.

Experimental Part

Preparation of 9-deoxo-9a-aza-11,12-desoxy-9a-homoerythromycin A 11,12-hydrogenorthoborate 89 g of 9-deoxo-6-desoxy-6,9-epoxy-9,9a-dihydro-9a-aza-homoerythromycin A are dissolved in 450 ml of methanol and cooled down between −5° and −10° C. While keeping the temperature in the specified interval 16 portions of 2.2 g each of sodium borohydride are added. Temperature and stirring conditions are maintained for two additional hours and the bulk of the reaction is allowed to reach 20° C. After 20 h, the methanol is evaporated to dryness. The residue is dissolved in 500 ml of methylene chloride and 750 ml of water and shaked for 30 min. The organic phase is separated and the aqueous phase is extracted with 250 ml of methylene chloride. The organic phases are combined, filtered over celite, dried with anhydrous sodium sulphate and concentrated to dryness to yield 85 g of 9-deoxo-9a-aza-11,12-desoxy-9a-homoerythromycin A 11,12-hydrogenorthoborate.

| IR (KBr) | $v_{max}$ = 3500, 2980, 2960, 1730, 1470, 1390, 1170, 1090, 1060 cm$^{-1}$ |
|---|---|
| $^1$H-NMR (CDCl$_3$) (partial) | δ = 2.21 (NMe$_2$), 3.27 (OMe) ppm. |
| $^{13}$C-NMR (CDCl$_3$) (partial) | δ = 180.0 (C=O), 79.63 (C$_{11}$), 76.46 (C$_{12}$) 58.7 (C$_{10}$), 57.1 (C$_9$), 49.4 (OMe), 40.2 (NMe$_2$) ppm |
| $^{11}$B-NMR (CDCl$_3$) | δ = 9.9 ppm ω$_{½}$ = 200 Hz |
| TLC | rf = 0.28 (petroleum ether : ethyl acetate: diethylamine 75:25:10) developer: ethanol/vanillin (sulphuric acid) |

Preparation of 9-deoxo-9a-aza-11,12-desoxy-9a-methyl-9a-home-erythromycin A 11,12-hydrogenorthoborate 50 of 9-deoxo-9a-aza-11,12-desoxy-9a-homoerythromycin a 11,12-hydrogenortho-borate are dissolved in 500 ml of chlorofrm, and subsequently a mixture of 5.5 ml of formic acid and 11.75 ml of equaous 35-40% formaldehyde is added. The reaction mixture is heated under pressure for 14 hours and subsequently cooled down to 15-20° C. 500 ml of water are added and the mixture is taken to pH=4 by adding 20% sulphuric acid. The mixture is taken for 15 min and the lower organic layer is separated. The alkaline equanous is extracted with 20×100 ml methylene cloride. The organic phase are combined and filtered over celite, dried with anhydrous sodium sulfate and evaporated tom dryness. The residue obtained is washed twice with 250 ml of ethyl ether yeilding a dry residue of 29 g of 9-deoxo-9a-aza-11,12-desoxy-9a-methyl-9a-homoerythromycin A 11,12-hydrogenorthoborate.

| IR (KBr) | $v_{max}$ = 3500, 1730, 1470, 1390, 1090, 1070, cm$^{-1}$ |
|---|---|
| $^1$H-NMR (CDCl$_3$) (partial) | δ = 2.00 (NMe$_2$), 2.30 (NMe), 3.37 (OMe) ppm |
| $^{13}$C-NMR (CDCl$_3$) (partial) | δ = 179.9 (C=O), 79.40 (C$_{11}$), 77.09 (C$_{12}$) 68.84 (C$_9$), 64.08 (C$_{10}$), 49.36 (OMe), 40.18 (NMe$_2$), 34.39 (NMe) ppm |
| $^{11}$B-NMR (CDCl$_3$) | δ = 10.1 ppm ω$_{½}$ = 180 Hz |
| m/e | M$^+$ = 775.5 |

-continued

| TLC | rf = 0.38 (petroleum ether : ethyl acetate: diethylamine 75:25:10) developer: ethanol/vanillin (sulphuric acid) |
|---|---|

Hydrolysis of 9-deoxo-9a-aza-11,12-desoxy-9a-methyl9a-homo-erythromycin A 11,12-hydrogenorthoborate. Synthesis of 9-deoxo-9a-aza-9a-methyl-9a-homo-erythromycin A (Azithromycin).

22 g of 9-deoxo-9a-aza-11,12-desoxy-9a-methyl-9a-homo-erythromycin A 11,12-hydrogenorthoborate are dissolved in 250 ml of acetonitrile to which 125 ml of water are subsequently added. 20% sulphuric acid is added to the mixture to take it to pH=2, and stirring is maintained for 30 min. The acidic solution is poured into a mixture of 350 ml of methylene chloride and 350 ml of water, immediately adding 48% lime until pH=9. The mixture is shaken for 15 min and the lower organic phase is separated. The alkaline aqueous phase is extracted with 2×100 ml of methylene chloride. The combined organic phases are filtered over celite and evaporated to dryness. The residue is dissolved in 50 ml of ethanol and 60 ml of water are added over 30 min. Precipitation is allowed for 2 h, and the solid is collected by filtration and vacuum-dried at 40° C. to yield 15 g of 9-deoxo-9a-aza-9a-methyl-9a-homo-erythromycin A (Azithromycin).

| IR (KBr) | $v_{max}$ = 3500, 3000, 2970, 1740, 1470, 1380, 1280, 1060 cm$^{-1}$ |
|---|---|
| $^1$H-NMR (CDCl$_3$) (partial) | δ = 2.31 (NMe$_2$), 2.34 (NMe), 3.38 (OMe) ppm |
| $^{13}$C-NMR (CDCl$_3$) (partial) | δ = 178.9 (C=O), 73.08 (C$_{12}$), 72.32 (C$_{11}$) 69.88 (C$_9$), 62.43 (C$_{10}$), 49.37 (OMe), 40.23 (NMe$_2$), 35.92 (NMe) ppm |
| m/e | M$^+$ = 749.5 |
| HPLC | corresponds according to USP XXIII |
| TLC | rf = 0.62 (petroleum ether : ethyl acetate: diethylamine 75:25:10) developer: ethanol/vanillin (sulphuric acid) |

Preparation of 9-deoxo-9a-aza-9a-methyl-9a-homoerythromycin A dihydrate. Method A 25 g of crystalline azithromycin monohydrate are dissolved in 130 ml of tert-butanol heating at 30° C. This solution is filtered and 130 ml of water are added over 6 h. The resulting mixture is taken to pH=11 by addition of NaOH 2N, cooled down below 10° C. and subsequently stirred for 48-72 h. The crystals are collected by filtration and dried (80 mm Hg/25° C.) to yield 15 g of azithromycin dihydrate.

Preparation of 9-deoxo-9a-aza-9a-methyl-9a-homoerythromycin A dihydrate. Method B 25 g of crystalline azithromycin monohydrate are dissolved in 50 ml of tert-butanol heating at 30° C. This solution is filtered and discharged over a mixture of 500 ml of petroleum ether and 20 ml of water. The resulting mixture is cooled down below 10° C. and subsequently stirred for 48–72 h. The crystals are collected by filtration and dried (80 mm Hg/25° C.) to yield 12 g of azithromycin dihydrate IR(KBr), $^1$H-NMR (CDCl$_3$), $^{13}$C-NMR (CDCl$_3$), m/e, TLC and HPLC are identical to those of the previous example.

Preparation of non-crystalline 9-deoxo-9a-aza-9a-methyl-9a-homoerythromycin A. Method A 5 g of crystalline azithromycin monohydrate are dissolved in 25 ml of tert-butanol heating at 30° C. This solution is filtered and solidified in a cooling bath. The solvent is sublimed at room temperature and 10$^{-2}$ mm Hg. The solid obtained is dried (80 mm Hg/40° C.) to yield 5 g of non-crystalline azithromycin.

IR (KBr) $v_{max}$=3500, 1740, 1470, 1280, 1268, 1257 cm$^{-1}$ (See FIG. 2) $^1$H-NMR (CDCl$_3$), $^{13}$C-NMR (CDCl$_3$), m/e, TLC and HPLC are identical to those of the previous example % H$_2$O (K. F.)=3.0% DSC=See FIG. 3 X-Ray Diffraction=See FIG. 4

Preparation of non-crystalline 9-deoxo-9a-aza-9a-methyl-9a-homoerythromycin A. Method B.

5 g of crystalline azithromycin monohydrate are dissolved in 25 ml of ethanol. The solution is filtered and the solvent evaporated at room temperature and 150 mm Hg. The solid obtained is dried (80 mm Hg/40° C.) to yield 5 g of non-crystalline azithromycin, which analytical data are identical to those of the previous example.

What is claimed is:

1. A method of preparing 9-deoxo-9a-aza-9a-methyl-9a-homoerythromycin A (Azithromycin) in a non-crystalline form, said method comprising:

forming a solution of Azithromycin in a solvent selected from the group consisting of aliphatic alcohols and cyclic ethers; and lyophilizing said solution, thereby preparing non-crystalline Azithromycin.

2. The method of claim 1, wherein the solvent is tert-butanol.

3. The method of claim 1, wherein the solvent is 1,4-dioxane.

4. A method of preparing Azithromycin in a crystalline dihydrate form, said method comprising:

dissolving Azithromycin in tert-butanol to form a solution; and combining said solution with water; thereby crystallizing Azithromycin as the crystalline dihydrate form.

5. The method of claim 4 further comprising, following the step of combining said solution with water, adjusting and cooling said solution.

6. A method of preparing Azithromycin in a crystalline dihydrate form, said method comprising:

dissolving Azithromycin in tert-butanol to form a solution; and combining said solution with a mixture of water and petroleum ether, thereby crystallizing Azithromycin as the crystalline dihydrate form.

7. The method of claim 6 further comprising, following the step of combining said solution with a mixture of water and petroleum ether, cooling said solution.

8. A method of preparing Azithromycin in a crystalline dihydrate form, said method comprising:

hydrolyzing 9-deoxo-9a-aza-11, 12-desoxy-9a-methyl-9a-homoerythromycin A 11, 12-hydrogenorthoborate in an organic solvent by contacting said 9-deoxo-9a-aza-11, 12-desoxy-9a-methyl-9a-homoerythromycin A 11, 12-hydrogenorthoborate with a dilute acid at room temperature and in pH range between 2 and 4, thereby producing Azithromycin;

dissolving said Azithromycin in tert-butanol to form a solution; and combining said solution with water, thereby crystallizing Azithromycin as the crystalline dihydrate form.

9. The method of claim 8 further comprising, following the step of combining said solution with water, adjusting and cooling said solution.

10. The method of claim 8, wherein the organic solvent is selected from the group consisting of ethyl acetate, acetonitrile, methanol, and ethanol.

11. The method of claim 8, wherein the dilute acid is selected from the group consisting of sulfuric acid, hydrochloric acid, and oxalic acid.

12. A method of preparing Azithromycin in a crystalline dihydrate form, said method comprising:

hydrolyzing 9-deoxo-9a-aza-11, 12-desoxy-9a-methyl-9a-homoerythromycin A 11, 12-hydrogenorthoborate in an organic solvent by contacting said 9-deoxo-9a-aza-11, 12-desoxy-9a-methyl-9a-homoerythromycin A 11, 12-hydrogenorthoborate with a dilute acid at room temperature and in pH range between 2 and 4, thereby producing Azithromycin;

dissolving said Azithromycin in tert-butanol to form a solution; and combining said solution with a mixture of water and petroleum ether, thereby crystallizing Azithromycin as the crystalline dihydrate form.

13. The method of claim 1 urther comprising, following the step of combining said solution with a mixture of water and petroleum ether, cooling said solution.

14. The method of claim 12, wherein the organic solvent is selected from the group consisting of ethyl acetate, acetonitrile, methanol, and ethanol.

15. The method of claim 12, wherein the dilute acid is selected from the group consisting of sulfuric acid, hydrochloric acid, and oxalic acid.

16. A method of preparing Azithromycin in a non-crystalline form, said method comprising:

hydrolyzing 9-deoxo-9a-aza- 11, 12-desoxy-9a-methyl-9a-homoerythromycin A 11, 12-hydrogenorthoborate in an organic solvent by contacting said 9-deoxo-9a-aza-11, 12-desoxy-9a-methyl-9a-homoerythromycin A 11, 12-hydrogenorthoborate with a dilute acid at room temperature and in pH range between 2 and 4, thereby producing Azithromycin;

forming a solution of said Azithromycin in tert-butanol; and lyophilizing said solution, thereby preparing non-crystalline Azithromycin.

17. The method of claim 16, wherein the organic solvent is selected from the group consisting of ethyl acetate, acetonitrile, methanol, and ethanol.

18. The method of claim 16 wherein the dilute acid is selected from the group consisting of sulfuric acid, hydrochloric acid, and oxalic acid.

* * * * *